US012667526B1

(12) United States Patent
Welch

(10) Patent No.: US 12,667,526 B1
(45) Date of Patent: Jun. 30, 2026

(54) METHOD OF ENCOURAGING GROWTH AND REGROWTH OF HAIR IN HUMAN MALES

(71) Applicant: James D. Welch, Omaha, NE (US)

(72) Inventor: James D. Welch, Omaha, NE (US)

( * ) Notice: Subject to any disclaimer, the term of this patent is extended or adjusted under 35 U.S.C. 154(b) by 481 days.

(21) Appl. No.: 18/445,368

(22) Filed: Aug. 4, 2023

Related U.S. Application Data

(63) Continuation-in-part of application No. 17/803,532, filed on Aug. 15, 2022, now Pat. No. 11,744,788.

(60) Provisional application No. 63/360,760, filed on Oct. 27, 2021.

(51) Int. Cl.
A61K 8/04 (2006.01)
A61Q 5/02 (2006.01)

(52) U.S. Cl.
CPC ................ A61K 8/044 (2013.01); A61Q 5/02 (2013.01); A61K 2800/805 (2013.01); A61K 2800/81 (2013.01); A61K 2800/92 (2013.01)

(58) Field of Classification Search
None
See application file for complete search history.

(56) References Cited

U.S. PATENT DOCUMENTS

| | | | | |
|---|---|---|---|---|
| 5,037,643 | A * | 8/1991 | Green | A61Q 7/00 514/20.7 |
| 6,596,266 | B2 * | 7/2003 | Catalfo | A61Q 7/00 424/727 |
| 6,666,878 | B2 * | 12/2003 | Carlgren | A61N 5/0617 607/91 |
| 8,088,123 | B2 * | 1/2012 | Kinoshita et al. | |
| 8,192,473 | B2 * | 6/2012 | Tucker et al. | |
| 8,609,072 | B2 * | 12/2013 | Florence et al. | |
| 8,834,940 | B2 * | 9/2014 | Trigiante | |
| 8,877,762 | B2 * | 11/2014 | Hu et al. | |
| 8,927,554 | B2 * | 1/2015 | Hu et al. | |
| 9,006,291 | B2 * | 4/2015 | Brinkenhoff | |
| 9,125,936 | B2 * | 9/2015 | Meyer et al. | |
| 9,408,795 | B2 * | 8/2016 | Duggan et al. | |
| 9,532,941 | B2 * | 1/2017 | Shapiro et al. | |
| 9,956,156 | B2 * | 5/2018 | Wo | |
| 9,962,360 | B2 * | 5/2018 | Miller et al. | |
| 9,962,444 | B2 * | 5/2018 | Malek | |
| 10,420,962 | B2 * | 9/2019 | Holmes | |
| 10,456,344 | B2 * | 10/2019 | Bhogal et al. | |
| 10,561,593 | B2 * | 2/2020 | Wu | |
| 10,688,030 | B2 * | 6/2020 | Nakano et al. | |
| 10,688,037 | B1 * | 6/2020 | Morely et al. | |
| 10,925,824 | B2 * | 2/2021 | Wo | |
| 11,000,466 | B2 * | 5/2021 | Wu | |
| 11,033,473 | B2 * | 6/2021 | Okunishi et al. | |
| 11,039,996 | B2 * | 6/2021 | Wu | |
| 11,052,059 | B2 * | 7/2021 | Schmidt | |
| 11,110,272 | B2 * | 9/2021 | Ingman et al. | |
| 11,116,770 | B2 * | 9/2021 | Sinclair | |
| 2009/0258085 | A1 * | 10/2009 | Bach et al. | |
| 2011/0087310 | A1 * | 4/2011 | Chen et al. | |
| 2012/0065708 | A1 * | 3/2012 | Kinoshita et al. | |
| 2013/0041432 | A1 * | 2/2013 | Tucker et al. | |
| 2022/0331223 | A1 * | 10/2022 | Falco | A61K 8/735 |

OTHER PUBLICATIONS

Strange Biological Activator Nourishes Aging Hair Follicles, Re Nourish Email Materials.*

* cited by examiner

*Primary Examiner* — Nannette Holloman

(74) *Attorney, Agent, or Firm* — James D. Welch

(57) ABSTRACT

Methodology for encouraging hair growth in male humans, and more particularly methodology which involves application of electromagnetic radiation, in functional combination with application of powdered and liquid materials and vibrations in hair challenged areas of a scalp.

23 Claims, No Drawings

METHOD OF ENCOURAGING GROWTH AND REGROWTH OF HAIR IN HUMAN MALES

METHOD OF ENCOURAGING GROWTH AND REGROWTH OF HAIR IN HUMAN MALES

This Application is a CIP of Allowed application Ser. No. 17/803,532, filed Aug. 15, 2022 and therevia Claims Benefit of 61/360,760 Filed Oct. 27, 2021.

TECHNICAL AREA

The present invention relates to methodology for encouraging hair growth in male humans, and more particularly to methodology for causing regrowth of hair therein involving application of electromagnetic radiation in functional combination with application of powdered and liquid materials and vibrations.

BACKGROUND

During the isolation of the Pandemic the Inventor herein, having a researcher's nature and having experienced typical male hair loss over the years, turned his attention to various approaches and materials applicable to achieving hair regrowth.

It is documented that Hair loss in Humans Males well known, and probably equally well resented by most of those afflicted, which includes, as mentioned, the Inventor herein. Decades ago he noticed a thinning of his hair, and adopted use of Minoxidil. That seemed to slow the hair loss, but did not stop it. A few years ago he bought one of the helmets with about 120 sources (LEDs/Lasers) of electromagnetic radiation (650 nm wavelength, 5mw's each) present therein. Use thereof did lead to some noticeable hair regrowth rather quickly. Recently he added application of Castor oil and essential Peppermint oil to the Minoxidil, and noticed added benefit. Very recently he added applying a single choice or a mixture of selections from the group consisting of powdered saw palmetto; powdered horsetail; powdered *equisetum arvense*; powdered fenugreek seed; powdered horny goat weed; powdered *pueraria* lobate; powdered *tribulus terrestris*; powdered ashwagandha; powdered cayenne; powdered habenero; powdered green tea; powdered sage; powdered ginger; powdered stinging nettles; powdered *gingko biloba*; powdered myrrh; powdered alpha-hydroxy; powdered *aloe vera*; powdered wheat protein; powdered wheat starch; casein; powdered keratin, powdered folic acid and powdered biotin, powdered stinging nettles; powdered *eclipta alba*; powdered centrella *asiatica*; powdered *phyllanthus emblica* etc.; are present in substantially equal, or exactly equal amounts by weight, and yet again noticed an improvement.

Most recently, upon realizing that the procedure involving application of electromagnetic radiation and the various topical liquids and powdered materials was not particularly successful in re-growing hair on the frontal portion of his scalp, he has adopted application of vibrations from a hand held vibrator to said frontal scalp areas and generally to the frontal and rearward portions of his scalp. Again, this procedure on its own, is not unknown.

Known relevant Patents and Published Application that describe application of electromagnetic radiation and various oils and powdered materials to hair challenged areas of a male human scalp are include 9,125,9361; 10,688,030; 11,033,473; 8,088,123; 8,192,473; 2011/0087310; 2012/

0065708 and 2013/0041432; 11,039,996; 11,052,059; 11,000,466; 11,110,272; 10,925,824; 11,116,770; 10,688, 030; 10,688,032; 10,456,344; 10,561,593; 10,420,962, 8,609,072; 9,956,156; 9,962,444; 9,962,360; 9,408,7951 9,532,941; 9,125,936; 8,877,762; 8,877,762; 9,006,291; 8,927,554 and 8,834,940. Further a simple Ebay Search for Hair Regrowth Caps and Helmets will turn-up many commercially available products.

It is mentioned in particular that Minoxidil has been shown to encourager hair growth in human males. Not so well known, but known, is that peppermint oil, ginger oil and lavender oil etc. also encourages such. And it is further known that castor bean oil encourages human hair growth.

The present invention is not found in a specific step, but rather is found in practicing a combination of steps involving application of electromagnetic radiation and substances known to encourage human male hair growth, in a manner that combines benefits of each. The Examiner of parent application Ser. No. 17/803,532 commented in her reasons for Allowance, that Bach, US-2009-0258085 seemed to be the closet Prior Art, but it did not provide anything that would led one skilled in the art to apply electromagnetic radiation to a scalp in combination with various components such as Castor Bean, Jojoba, Vitamines, Mint Oli, Cumin Oil, Ginger Oil, Tea Tree Oil and Lavender Oil.

Even in view of the extensive literature in the area, need remains for easy to practice methodology, practice of which encourages hair growth, and/or regrowth in human males.

DISCLOSURE OF THE INVENTION

The present Invention is a method of encouraging hair growth in male humans, comprising, in functional combination the steps of:

a) providing a male human scalp comprising at least one hair challenged area;

b) in a functional sequence, regarding said hair challenged area:

1) applying electromagnetic radiation for at least five minutes;

2) providing and applying at least one powdered material; and 3) providing and applying at least one liquid.

The step b) providing of and applying a powdered material can involve providing and applying at least some of at least one selection from the group consisting of:

powdered horny goat weed;
powdered *pueraria* lobate;
powdered *tribulus terrestris;*
powdered ashwagandha;
powdered cayenne;
powdered habenero;
powdered green tea;
powdered sage;
powdered *gingko biloba;*
powdered myrrh;
powdered alpha-hydroxy;
powdered *aloe vera;*
powdered folic acid;
powdered casein;
powdered keratin;
powdered biotin;
powdered *ginseng* Root;
powdered vetiver grass;
powdered caffeine;
powdered Co-enzyme Q;
powdered folate;

powdered gotukola leaf;
powdered milk thistle;
powdered African pygeum;
powdered niacinamide (NAD) and/or niacin;
powdered *nigella sativa;*
powdered *eclipta alba;*
powdered centrella *asiatica;*
powdered *phyllanthus emblica;*
powdered turmeric;
powdered curcumin;
powdered pine bark;
powdered casein;
powdered buckthorn;
powdered burdock;
powdered chamomile;
powdered comfrey;
powdered hops;
powdered rosemary;
powdered thyme;
powdered yarrow;
powdered *yucca;*
powdered calendula;
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
Powdered black pepper;
powdered riboflavin; and
powdered thiamine.

The step b) providing of and applying a liquid can involve providing and applying at least some of at least one selection from the group consisting of:
minoxidil infused liquid:
Mint infused liquid;
ginger infused liquid;
lavender infused liquid;
castor bean infused liquid;
jojoba infused liquid;
*malaleuca* infused liquid;
cumin infused liquid;
D-alpha tocopherol (vitamin E) infused liquid;
caffeine infused liquid;
biotin infused liquid;
folic acid infused liquid;
*eucalyptus* liquid;
lemongrass liquid argan liquid;
clove liquid; and
hyaluronic acid.
Said method can further include in step b):
4) applying a cream or ointment to said at least one hair challenged area.
5) shampooing said male human scalp with a shampoo comprising at least some of at least one selection from the group consisting of:
mint;
cayenne;
caffeine;
saw palmetto;
horsetail;
*equisetum arvense*; and
biotin;
6) providing a vibrator and apply vibrations to a hair challenged area of a provided scalp.

It is to be understood that the various categories 1), 2), 3), 4), 5) and 6) do not imply any specific order in the practice thereof. It is rather that practice of them is undertaken. No known Prior Art suggests such an integrated procedure. There are preferred orders of practicing the various categories and some of them are presented following. A functional sequence for Step b) categories might be 5), 3), 1), 2), 4) and 6), with time being provided between 3) and 1) for hair to dry. Other sequences are within the scope of the Present Invention. However the sequence of practicing the categories in step b) could involve a sequence of 1), 3) 2) or 1), 2) 3) or 3), 1,2).

Also, it is, of course necessary to practice the method a multiplicity of times to achieve hair regrowth. A practitioner should commit to a daily practice for years to obtain best results. It is also advisable to begin practice of the methodology as soon as hair loss is noted. Delay allows hair follicles to become dormant and very difficult to revive. The Inventor, aged 77, has noticed that obviously viable follicles respond fairly quickly, but that areas which have been without much hair for a long time are very slow to respond. However, slowly even such areas do show progress.

One Present Invention Method of encouraging hair growth in male humans which prescribes an ordered practice of at least some of the categories 1), 2), 3), 4), 5) and 6), comprises, in functional combination, the steps of:
a) providing a male human scalp comprising at least one hair challenged area;
b) shampooing said male human scalp with a shampoo comprising at least some of one selection from the group consisting of:
mint;
cayenne;
caffeine;
saw palmetto;
horsetail;
*equisetum arvense*; and
biotin;
c) while still wet, applying at least one selection from the group consisting of:
powdered saw palmetto;
powdered horsetail;
powdered *equisetum arvense;*
powdered ginger;
powdered stinging nettles;
powdered cayenne;
powdered casein;
powdered keratin;
powdered folic acid;

powdered biotin;
powdered buckthorn;
powdered burdock;
powdered chamomile;
powdered comfrey;
powdered hops;
powdered rosemary;
powdered thyme;
powdered yarrow;
powdered yucca;
powdered calandula;
powdered PABA;
powdered peony root;
powdered barley grass;
powdered silicon dioxide;
powdered basil;
powdered MACA;
powdered sarsaparilla;
powdered muira poama;
Powdered pantothenic acid;
   powdered Japanese knotweed;
   powdered resveratrol;
   powdered niacin;
   powdered molybdenum;
   powdered selenium;
   powdered manganese;
   powdered potassium;
   powdered calcium;
   powdered iron;
   powdered copper;
   powdered iodine;
   powdered chromium;
   powdered collagen;
   powdered hydrolyzed collagen;
   powdered keratin;
   powdered solubilized keratin;
   powdered black pepper;
   powdered riboflavin; and
   powdered thiamine;
and also while still wet, applying a mixture of substantially or exactly equal amounts of minoxidil solution and at least one selection from the group consisting of:
   Mint infused liquid;
   ginger infused liquid;
   lavender infused liquid;
   castor bean infused liquid;
   jojoba infused liquid;
   malaleuca infused liquid;
   cumin infused liquid;
   D-alpha tocopherol (vitamin E) infused liquid;
   caffeine infused liquid;
   biotin infused liquid;
   folic acid infused liquid;
   eucalyptus liquid;
   lemongrass liquid
   argan liquid;
   clove liquid; and
   hyaluronic acid;
d) while said male human scalp is still wet, or after it has dried, providing a multiple electromagnetic radiation source containing helmet or cap and applying electromagnetic radiation provided thereby for at least five minutes to said at least one hair challenged area of said scalp while at least one of the multiple electromagnetic radiation sources are energized; and
e) after said male human scalp has dried applying at least one selection from the group consisting of:

powdered horny goat weed;
powdered pueraria lobate;
powdered tribulus terrestris;
powdered ashwagandha;
powdered cayenne;
powdered habenero;
powdered green tea;
powdered sage;
powdered gingko biloba;
powdered myrrh;
powdered alpha-hydroxy;
powdered aloe vera;
powdered folic acid;
powdered casein;
powdered keratin;
powdered biotin;
powdered ginseng Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered nigella sativa;
powdered eclipta alba;
powdered centrella asiatica;
powdered phyllanthus emblica;
powdered turmeric;
powdered curcumin; and
powdered pine bark;
powdered casein;
powdered buckthorn;
powdered burdock;
powdered chamomile;
powdered comfrey;
powdered hops;
powdered rosemary;
powdered thyme;
powdered yarrow;
powdered yucca;
powdered calendula;
powdered PABA;
powdered peony root;
powdered barley grass;
powdered silicon dioxide;
powdered basil;
powdered MACA;
powdered sarsaparilla;
powdered muira poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;

powdered solubilized keratin;
powdered black pepper;
powdered riboflavin; and
powdered thiamine;
f) at some point after step a) providing and applying a
cream or ointment (eg. a transforming growth factor
(TGF Beta) containing cream to said at least one hair
challenged area.

It is noted that minoxidil is typically available in a 5% solution and that other liquids typically are available in higher concentrations in oil or water. The present invention is not limited by requiring specific concentrations, but only in provision if at least some of a recited selected component.

Another recital of a Present Invention method of encouraging hair growth in male human's, comprises the steps of:
a) providing and shampooing a scalp of a human male
having at least one hair challenged area in need of hair
regrowth, along with any hair present, with a shampoo
comprising at least some of at least one selection from
the group consisting of:
mint;
cayenne;
caffeine;
saw palmetto;
horsetail;
*equisetum arvense*; and
biotin;
present therein.
The Method provides that:
b) before drying said scalp providing and applying a
mixture of substantially or exactly equal amounts of at
least two selections from the group consisting of:
powdered saw palmetto;
powdered horsetail;
powdered *equisetum arvense;*
powdered ginger;
powdered stinging nettles;
powdered cayenne;
powdered casein;
powdered keratin;
powdered folic acid;
powdered biotin;
to said at least one hair challenged area of said provided
scalp.
Next, the Method provides for:
c) providing and applying a mixture of substantially or
exactly equal amounts of minoxidil solution from a 5%
source and at least one selection from the group con-
sisting of:
mint infused liquid;
ginger infused liquid;
lavender infused liquid;
castor bean infused liquid;
jojoba infused liquid;
*malaleuca* infused liquid;
cumin infused liquid;
D-alpha tocopherol (vitamin E) infused liquid;
caffeine infused liquid;
biotin infused liquid;
folic acid infused liquid;
*eucalyptus* liquid;
lemongrass liquid
argan liquid;
clove liquid; and
hyaluronic acid;
to said at least one hair challenged area of said provided
scalp.

And the Method continues with:
d) drying said scalp and any hair present, then providing
and applying a mixture of substantially or exactly equal
amounts of at least two selections from the group
consisting of:
powdered saw palmetto;
powdered horsetail;
powdered *equisetum arvense;*
powdered ginger;
powdered stinging nettles;
powdered cayenne;
powdered casein;
powdered keratin;
powdered folic acid;
to said at least one hair challenged area of said provided
scalp.
Importantly, the Method continues with:
e) providing a multiple electromagnetic radiation source.
containing helmet or cap and applying electromagnetic
radiation provided thereby for at least five minutes to
said at least one hair challenged area of said scalp while
at least one of the multiple electromagnetic radiation
sources are energized.
At some point in the Method:
f) after step a) providing and applying a cream or ointment
(eg. a transforming growth factor (TGF Beta) contain-
ing cream to said at least one hair challenged area.

In the just recited method all selections in the groups b), c) and d) can be present in substantially, or exactly equivalent amounts in each group.

Any recited method recited above, can further comprise orally ingesting at least some of at least one selection from the group consisting of:
saw palmetto;
horsetail;
*equisetum arvense;*
ginger;
stinging nettles;
casein;
keratin;
peppermint;
ginger;
lavender oil;
vitamin E;
biotin;
cumin;
castor oil;
jojoba oil;
*malaleuca* oil;
cumin oil;
D-alpha tocopherol (vitamin E);
fenugreek seed;
horny goat weed;
*pueraria* lobate;
*tribulus terrestris;*
ashwagandha;
cayenne;
habenero;
green tea;
sage;
*gingko biloba;*
myrrh;
alpha-hydroxy;
*aloe vera;*
folic acid;
biotin;
*ginseng* Root;

vetiver grass;

caffeine;

Co-enzyme Q;

folate;

gotukola leaf;

milk thistle;

African pygeum;

niacinamide (NAD) and/or niacin;

*nigella* satavia;

*eclipta alba;* centrella *asiatica;*

*phyllanthus emblica;* turmeric;

curcumin;

pine bark;

caesin;

cayenne;

powdered buckthorn;

powdered burdock;

powdered chamomile;

powdered comfrey;

powdered hops;

powdered rosemary;

powdered thyme;

powdered yarrow;

powdered *yucca;* powdered *calendula;* powdered PABA;

powdered peony root;

powdered barley grass;

powdered silicon dioxide;

powdered basil;

powdered MACA;

powdered *sarsaparilla;* powdered *muira* poama;

powdered pantothenic acid;

powdered Japanese knotweed;

powdered resveratrol;

powdered niacin;

powdered molybdenum;

powdered selenium;

powdered manganese;

powdered potassium;

powdered calcium;

powdered iron;

powdered copper;

powdered iodine;

powdered chromium;

powdered collagen;

powdered hydrolyzed collagen;

powdered keratin;

powdered solubilized keratin;

powdered black pepper;

powdered riboflavin; and powdered thiamine;

at least one vitamin selected from the group of: A; C; D1; D2; D3; B3; B5; K and B12;

at least one amino acid selected from the group of: alanine; cysteine; tryptophan; glutamic acid; histidine; isoleucine; tryptophan; arginine; aspartic acid; threonine; tyrosine; glycine; leucine; proline; lysine; methionine; serine; valine and phenylalanine.

Again, any above recited can further comprise providing a vibrator and apply vibrations to a hair challenged area of a provided scale.

To provide additional insight the following is included. Disclosure from Parent Application Ser. No. 17/803,532.

The restoration of hair in human males, in the inventor's experience, must be divided into two parts. First, what works on the rearward portion of the upper human male scalp, and second, what works on the forward portion thereof.

Reward Portion of Scalp

The present invention is a sequence of steps that apply existing sources of electromagnetic radiation, along with minoxidil, mint oil (preferably menthol containing essential peppermint oil), castor bean oil and an additional known single substance, or mixtures of known substances selected from a group consisting of: powdered saw palmetto; powdered horsetail; powdered *equisetum arvense*; powdered fenugreek seed; powdered horny goat weed; powdered *pueraria* lobate; powdered *tribulus terrestris*; powdered ashwagandha; powdered cayenne; powdered habenero; powdered green tea; powdered sage; powdered ginger; powdered stinging nettles; powdered *gingko biloba*; powdered myrrh; powdered alpha-hydroxy; powdered *aloe vera*; powdered wheat protein; powdered wheat starch; powdered casein; powdered keratin, powdered folic acid and powdered biotin powdered zinc; powdered *ginseng* root; powdered niacinamide (NAD) and/or niacin and powdered *nigella sativa* powdered *eclipta alba*; powdered centrella *asiatica*; and powdered *phyllanthus emblica.*

Where more than one selection is made, a mixture of said powdered selections can be arrived at by providing, by weight, substantially equal amounts of each selection, exact percentages of said powdered selections being limited only in that they sum to 100% in total. Further, said single selection or a mixture of said selections is considered as a unit on par with the minoxidil, peppermint oil and castor bean oil on a volume basis. This can be appreciated by considering that a single application might be comprised of a half a teaspoon of each of the minoxidil, mint oil, cumin oil and castor oil, cumin oil, D-alpha tocopherol (vitamin E) infused oil, biotin infused oil as well as a similar amount of a single selection, or mixture of more than one selection from the above list of powdered selections. It is noted that the half teaspoon measure, or a bit less, is appropriate as a single usage dosage for evident typical male pattern baldness.

The present invention has been arrived at empirically by the inventor over a period of many years by trial and evaluation of results achieved, and has benefitted him. The results of practicing the invention methodology by the inventor, has improved his hair growth over said period of many years, especially in the rearward areas of his scalp.

The present invention can be recited as a method of encouraging hair growth in male humans, comprising the steps of:

in either order practicing steps a) and b):

a) providing a human scalp comprising at least one hair challenged area in need of hair regrowth;

b) providing a multiple electromagnetic radiation source containing helmet or cap suitable for placement adjacent to at least said at least one hair challenged area of said human scalp, a vibrator for producing vibrations and liquid sources of minoxidil, mint oil from a substantially or exactly 100% source thereof; ginger oil from a substantially or exactly 100% source thereof; lavender oil from a substantially or exactly 100% source thereof; castor bean oil from a substantially or exactly 100% source thereof; jojoba oil from a substantially or exactly 100% source thereof; *malaleuca* oil from a substantially pure if not per se. 100% pure source thereof; cumin oil from a substantially or exactly 100% source thereof; D-alpha tocopherol (vitamin E) infused oil; and biotin infused oil.

The method proceeds with, in either order, practicing steps c) and d):

c) applying electromagnetic radiation provided by said multiple electromagnetic radiation source containing helmet or cap for at least 5 minutes to said at least one hair challenged area while at least one of the multiple electromagnetic radiation sources are energized;

d) applying to said at least one hair challenged area, and leaving it in place, a volume of liquid comprising at least one selection from the group consisting of:

minoxidil solution from a 5% source;

mint oil from a substantially or exactly 100% source thereof;

ginger oil from a substantially or exactly 100% source thereof;

lavender oil from a substantially or exactly 100% source thereof;

castor bean oil from a substantially or exactly 100% source thereof;

jojoba oil from a substantially or exactly 100% source thereof;

*malaleuca* oil from a substantially pure if not per se. 100% pure source thereof;

cumin oil from a substantially or exactly 100% source thereof;

D-alpha tocopherol (vitamin E) infused oil; and biotin infused oil;

exact amounts of each selection being limited only in that they sum to 100% by volume in total.

The method can further involve, at some point after steps b) use of the vibrator to apply vibrations to the at least one hair challenged area.

Preferably said method is repeated on a daily basis for a period of years. In the inventor's experience, it is disclosed, that the methodology disclosed herein cannot be expected to provide immediate results on a time scale of days, but rather over a period of years.

Said method can further involve that step d) mint oil comprises at least 1% liquid menthol by volume, such as essential peppermint oil, which is preferred.

Said method can further involve that the step d) components of minoxidil, mint oil; ginger oil; lavender; castor bean oil; jojoba oil; *malaleuca* oil; cumin oil; D-alpha tocopherol (vitamin E) infused oil; and biotin infused oil components are present in substantially equal, or exactly equal amounts by volume.

The method can also involve, including in the step d) at least an equal amount by volume, at least one selection from the consisting of:

powdered saw palmetto;

powdered horsetail;

powdered *equisetum arvense;* powdered fenugreek seed;

powdered horny goat weed;

powdered *pueraria* lobate;

powdered *tribulus terrestris;* powdered ashwagandha;

powdered cayenne;

powdered habenero;

powdered green tea;

powdered sage;

powdered ginger;

powdered stinging nettles;

powdered *gingko biloba;* powdered myrrh;

powdered alpha-hydroxy;

powdered *aloe vera;* powdered wheat protein;

powdered wheat starch;

powdered casein;

powdered keratin;

powdered folic acid;

powdered biotin;

powdered zinc;

powdered *ginseng* Root;

powdered vetiver grass;

powdered caffeine;

powdered Co-enzyme Q;

powdered folate;

powdered gotukola leaf;

powdered milk thistle;

powdered African pygeum;

powdered niacinamide (NAD) and/or niacin;

powdered *nigella sativa;* powdered *eclipta alba;* powdered centrella *asiatica;* powdered *phyllanthus emblica;* powdered turmeric;

powdered curcumin; and powdered pine bark;

wherein, when more than one selection is made a mixture of said selections is arrived at by providing, by weight, approximately equal amounts of each selection. Exact percentages of said powdered selections being limited only in that they sum to 100% in total, said single selection or a mixture of said selections is considered as a unit on par with the minoxidil etc.

Preferably equal weights of each powdered selection should determine the amount of each, but for the purposes of this invention equal weights can be approximated by providing about half a teaspoon of each selection.

It is clarified that one can make selections from the step d) selection group of powders (when included) then measure out weights of each selected powder and mix the volumes of said selections. A volume thereof is added to the volumes of each of the minoxidil, mint and castor oil from step c) volumes is then sequestered from the mixture of powders. A preferred, but not exclusive, practice is to make volumes of the various components approximately equal.

The step d) components, and when present one or more selections from the group of powdered saw palmetto; powdered horsetail; powdered *equisetum arvense;* powdered fenugreek seed; powdered horny goat weed; powdered *pueraria* lobate; powdered *tribulus terrestris;* powdered ashwagandha; powdered cayenne; powdered habenero; powdered green tea; powdered sage; powdered ginger; powdered stinging nettles; powdered *gingko biloba;* powdered myrrh; powdered alpha-hydroxy; powdered *aloe vera;* powdered wheat protein; powdered wheat starch; powdered casein; powdered keratin, powdered folic acid and powdered biotin powdered stinging nettles; powdered *eclipta alba;* powdered centrella *asiatica;* powdered *phyllanthus emblica* in total, can be present in substantially equal, or exactly equal amounts by volume. For instance, each of the minoxidil, mint oil, ginger oil, lavender oil, cumin oil and castor oil; jojoba oil; *malaleuca* oil; cumin oil; D-alpha tocopherol (vitamin E) infused oil; and biotin infused oil and a unit of the single selection, or a mixture of more than one selection from the list of powdered materials as a unit, can all be of a volume equivalent of a half tea spoon, for application to an area of a human male scalp typical in male pattern baldness. Where a volume greater than appropriate for application to a hair challenged area of a human male scalp is prepared, a volume of the combined components appropriate for application, (eg. two teaspoons in the case of early male pattern baldness) can be sequestered in each individual application.

Said method can involve that at least one of the multiple electromagnetic radiation sources provide a wavelength of 650 nm, (although benefits can be achieved using between about 600 and 1000 nm) at least, and in which step c) is practiced for a time selected from the group consisting of:

at least 0.5 hours;
at least 1.0 hours;
at least 1.5 hours; and
at least 2.0 hours.

(Note, during the pandemic the inventor has, on a daily basis when time allowed, routinely applied a helmet containing about 120 Laser/LED's that provide electromagnetic radiation of a 650 nm wavelength at 5 mw (other wavelengths and wattages are possible and should be considered as included in the Claims) to his scalp for 1.5 hours or longer at a time, which seemed to be very beneficial).

The method can involve that, with or without practice of step c) more than once, that any of the variants of the step d) mixture is applied to the at least one hair challenged area at least twice a day.

Further, said method can involve, prior to step a) shampooing scalp and any hair present, and while wet providing and applying approximately equal amounts of minoxidil from a 5% solution thereof, and essential peppermint oil, ginger oil, lavender oil, cumin oil and castor oil from 100% sources thereof; and when the shampooed scalp and any hair present is substantially dry, providing and applying at least 1% by volume at least one selection from the group consisting of:

powdered saw palmetto;
powdered horsetail;
powdered *equisetum arvense;*
powdered fenugreek seed;
powdered horny goat weed;
powdered *pueraria* lobate;
powdered *tribulus terrestris;*
powdered ashwagandha;
powdered cayenne;
powdered habenero;
powdered green tea;
powdered sage;
powdered ginger;
powdered stinging nettles;
powdered *gingko biloba;*
powdered myrrh;
powdered alpha-hydroxy;
powdered *aloe vera;*
powdered wheat protein;
powdered wheat starch;
powdered casein;
powdered keratin;
powdered folic acid;
powdered biotin;
powdered zinc;
powdered *ginseng* Root;
powdered vetiver grass;
powdered caffeine;
powdered Co-enzyme Q;
powdered folate;
powdered gotukola leaf;
powdered milk thistle;
powdered African pygeum;

powdered niacinamide (NAD) and/or niacin;
powdered *nigella sativa;*
powdered *eclipta alba;*
powdered centrella *asiatica;*
powdered *phyllanthus emblica;*
powdered turmeric;
powdered curcumin; and
powdered pine bark;

wherein when more than one selection is made a mixture of said selections is arrived at by providing, by weight, approximately equal amounts of each selection exact percentages of said powdered selections being limited only in that they sum to 100% in total; followed by styling any hair and leaving all materials applied in place.

Further, the method can comprise a step e) that involves providing access to substantially pure or pure per se., one or more selections from the group consisting of:

powdered saw palmetto;
powdered horsetail;
powdered *equisetum arvense;*
powdered fenugreek seed;
powdered horny goat weed;
powdered *pueraria* lobate;
powdered *tribulus terrestris;*
powdered ashwagandha;
powdered cayenne;
powdered habenero;
powdered green tea;
powdered sage;
powdered ginger;
powdered stinging nettles;
powdered *gingko biloba;*
powdered myrrh;
powdered alpha-hydroxy;
powdered *aloe vera;*
powdered wheat protein;
powdered wheat starch;
powdered casein;
powdered keratin;
powdered folic acid;
powdered biotin;
powdered zinc;
powdered *ginseng* Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *nigella sativa;*
powdered *eclipta alba;*
powdered centrella *asiatica;*
powdered *phyllanthus emblica;*
powdered turmeric;
powdered curcumin; and
powdered pine bark;

after step d) applying to said hair challenged area after the liquid in step d) has substantially dried said single selected powder or mixture of selected powders to said at least one region of hair challenged scalp and leaving it in place.

(Note, when applied to dry hair, powdered Keratin alone, or in mixture with other selections, can adhere to hair giving it a fuller appearance. A product from a Company named "Finally Hair Corp." markets a product for just that purpose, which is represented as containing selections from the group of keratin, Gossyplum *herbaceum* and polymers).

Said method can further comprise:

practicing steps f) and g) in either order:

f) applying electromagnetic radiation provided by a multiple electromagnetic radiation source containing helmet or cap for at least 5 minutes to said at least one hair challenged area while at least one of the multiple electromagnetic radiation sources are energized;

g) applying to said at least one hair challenged area, and leaving it in place, a liquid comprising at least one selection from the group consisting of:

minoxidil solution from a 5% source;

mint oil from a substantially pure if not per se. 100% pure source thereof;

ginger oil from a substantially pure if not per se. 100% pure source thereof;

lavender oil from a substantially or exactly 100% source thereof;

castor bean oil from a substantially pure if not per se. 100% pure source thereof;

jojoba from a substantially or exactly 100% source thereof oil;

*malaleuca* oil from a substantially pure if not per se. 100% pure source thereof;

cumin oil from a substantially pure if not per se. 100% pure source thereof;

D-alpha tocopherol (vitamin E) infused oil; and biotin infused oil;

exact amounts of each selection being limited only in that they sum to 100% in total by volume.

It is desirable that the step e) powdered selection(s) be left in place so that they remain when steps f) and g) are practiced. For instance, steps f) and g) can be practiced before retiring to bed at night, whereas step e) had been practiced earlier in the day. A morning shampooing is advisable however, to remove the oils, followed by a morning application of at least minoxidil and mint oil.

In the step g) mint oil can comprise at least 1.0-40% liquid menthol by volume, including essential menthol containing peppermint oil.

Said method can involve the components in step g) are present in substantially equal, or exactly equal amounts by volume Said method can involve at least one of the multiple electromagnetic radiation sources provide a wavelength of 650 nm at 5 mw's, and step g) is practiced for a time selected from the group consisting of:

at least 0.5 hours;

at least 1.0 hours;

at least 1.5 hours; and at least 2.0 hours.

(Note, at the beginning of practicing the present invention methodology a procedure might involve selecting 2.0 hours during the first three months, 1.5 hours during the second three months, 1.0 hour during the third three months and 0.5 hours in the fourth three months and perhaps even a shorter period thereafter).

Said method can provide that the step d) selections further include a volume of liquid comprising a "tea" made from steeping substantially equal amounts by volume of:

powdered saw palmetto;

powdered horsetail;

powdered *equisetum arvense;* powdered fenugreek seed;

powdered ginger;

powdered stinging nettles;

said "tea" optionally further comprising at least one selection from the group consisting of:

powdered horny goat weed;

powdered *pueraria* lobate;

powdered *tribulus terrestris;* powdered ashwagandha;

powdered cayenne;

powdered habenero;

powdered green tea;

powdered sage;

powdered *gingko biloba;* powdered myrrh;

powdered alpha-hydroxy;

powdered *aloe vera;* powdered folic acid;

powdered casein;

powdered keratin;

powdered biotin;

powdered *ginseng* Root;

powdered vetiver grass;

powdered caffeine;

powdered Co-enzyme Q;

powdered folate;

powdered gotukola leaf;

powdered milk thistle;

powdered African pygeum;

powdered niacinamide (NAD) and/or niacin;

powdered *nigella* satavia;

powdered *eclipta alba;* powdered centrella *asiatica;* powdered *phyllanthus emblica;* powdered turmeric;

powdered curcumin; and powdered pine bark;

in water, or an oil, (possibly heated up to 190 Degree F.) There are available small colanders produced for use with tea leaves, which work well for producing said "tea". Or one can just add hot water to the mixture of powders. In use a volume of said liquid "tea" applied to a hair challenged area of a human male scalp is the same as the volume of any other Step d) selection. In the alternative, an amount of a mixture of selected powdered materials can be directly applied to a wet scalp.

Another method of encouraging hair growth in male humans, comprising the steps of:

in either order practicing steps a) and b):

a) providing a human scalp comprising at least one hair challenged area in need of hair regrowth;

b) providing a multiple electromagnetic radiation source containing helmet or cap suitable for placement adjacent to at least said at least one hair challenged area of said human scalp, and liquid sources of minoxidil, mint oil, and castor bean oil, jojoba oil, *melaleuca* oil, and providing and applying at least one selection from the group consisting of:

powdered saw palmetto;

powdered horsetail;

powdered *equisetum arvense;* powdered fenugreek seed;

powdered horny goat weed;

powdered *pueraria* lobate;

powdered *tribulus terrestris;* powdered ashwagandha;

powdered cayenne;

powdered habenero;

powdered green tea;
powdered sage;
powdered ginger;
powdered stinging nettles;
powdered *gingko biloba;*
powdered myrrh;
powdered alpha-hydroxy;
powdered *aloe vera;*
powdered wheat protein;
powdered wheat starch;
powdered casein;
powdered keratin;
powdered folic acid;
powdered biotin;
powdered zinc;
powdered *ginseng* Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *nigella sativa;*
powdered *eclipta alba;*
powdered centrella *asiatica;*
powdered *phyllanthus emblica;*
powdered turmeric;
powdered curcumin; and
powdered pine bark;
wherein when more than one selection is made a mixture of said selections is arrived at by providing, by weight, equal amounts of each selection exact percentages of said powdered selections being limited only in that they sum to 100% in total;
c) shampooing said scalp, along with any hair present, of said human male;
d) while the scalp and any hair present are still wet, providing and applying approximately equal amounts of minoxidil from a 5% solution thereof, mint oil, ginger oil, lavender oil, cumin oil and castor oil, each of the later being from a substantially 100% source thereof;
e) when the scalp and any hair present are substantially dry applying said at least one selection from the group consisting of:
powdered saw palmetto;
powdered horsetail;
powdered *equisetum arvense;*
powdered fenugreek seed;
powdered horny goat weed;
powdered *pueraria* lobate;
powdered *tribulus terrestris;*
powdered ashwagandha;
powdered cayenne;
powdered habenero;
powdered green tea;
powdered sage;
powdered ginger;
powdered stinging nettles;
powdered *gingko biloba;*
powdered myrrh;
powdered alpha-hydroxy;
powdered *aloe vera;*
powdered wheat protein;
powdered wheat starch;

powdered casein;
powdered keratin;
powdered folic acid;
powdered biotin;
powdered zinc;
powdered *ginseng* Root;
powdered vetiver grass;
powdered caffeine;
powdered Co-enzyme Q;
powdered folate;
powdered gotukola leaf;
powdered milk thistle;
powdered African pygeum;
powdered niacinamide (NAD) and/or niacin;
powdered *nigella sativa;*
powdered *eclipta alba;*
powdered centrella *asiatica;*
powdered *phyllanthus emblica;*
powdered turmeric;
powdered curcumin; and
powdered pine bark;
wherein when more than one selection is made a mixture of said selections is arrived at by providing, by weight, approximately equal amounts of each selection exact percentages of said powdered selections being limited only in that they sum to 100% in total;
and not removing applied materials in steps d) and e);
said method further comprising:
f) applying electromagnetic radiation provided by said multiple electromagnetic radiation source containing helmet or cap for at least one-half hour to said at least one hair challenged area while at least one of the multiple electromagnetic radiation sources are energized.
Said method can, at some point after step b), involve using said vibrator to apply vibrations to said at least one hair challenged area for at least five minutes.
Said method can provide that the step d) selections further include a volume of liquid comprising a "tea" made from steeping substantially equal amounts by volume of:
powdered saw palmetto;
powdered horsetail;
powdered *equisetum arvense;*
powdered fenugreek seed;
powdered ginger;
powdered stinging nettles;
said "tea" optionally further comprising at least one selection from the group consisting of:
powdered horny goat weed;
powdered *pueraria* lobate;
powdered *tribulus terrestris;*
powdered ashwagandha;
powdered cayenne;
powdered habenero;
powdered green tea;
powdered sage;
powdered *gingko biloba;*
powdered myrrh;
powdered alpha-hydroxy;
powdered *aloe vera;*
powdered casein;
powdered keratin;
powdered folic acid;
powdered biotin;
powdered *ginseng* Root;
powdered vetiver grass;
powdered caffeine;

powdered Co-enzyme Q;

powdered folate;

powdered gotukola leaf;

powdered milk thistle;

powdered African pygeum;

powdered niacinamide (NAD) and/or niacin;

powdered *nigella sativa;* powdered *eclipta alba;* powdered centrella *asiatica;* powdered *phyllanthus emblica;* powdered turmeric;

powdered curcumin; and powdered pine bark;

in water, or an oil, (possibly heated to upwards of 190 degrees F.). The "tea" can also contain alcohol in a ratio of about 20:1.

There are available small colanders produced for use with tea leaves, which work well for producing said "tea", or one can just apply hot (eg. 190 degrees Fahrenheit) to the mixture of powders. In use a volume of said liquid "tea" applied to a hair challenged area of a human male scalp is the same as the volume of any other Step d) selection.

It is noted that measurements of "equal amounts" of, for instance minoxidil solution, mint oil (eg. essential peppermint), ginger oil, lavender oil, cumin oil and castor oil can be made with as simple a measuring system as a teaspoon. By simply estimating what constitutes half a teaspoon full for each of the components one can get good enough measurements. And where selection(s) from the group consisting of powdered horny goat weed; powdered *pueraria* lobate; powdered *tribulus terrestris*; powdered ashwagandha; powdered cayenne; powdered habenero; powdered green tea; powdered sage; powdered ginger; powdered stinging nettles; powdered *gingko biloba*; powdered myrrh; powdered alpha-hydroxy; powdered *aloe vera*; powdered wheat protein; powdered wheat starch; powdered casein; powdered keratin, powdered folic acid and powdered biotin are utilized is/are made, and which multiple selections are made, mixed together and considered as a unit, again the teaspoon volume approach can be applied. In practice Inventor Welch has used an approach of simply pouring approximately amounts of each component into a jar and mixing them, then pouring about a teaspoon full into his cupped left hand and applying it to his hair challenged scalp area. That is to say, "exact" equivalence of amounts is, of course, not required in practice of the methodology, and the Claims should be understood to reflect said basic reality.

Also, the terminology Casein is to be taken to possibly include amino-acids and proteins, especially those common in hair, (eg. Cysteine, Cystine, Arginine, Methionine, Tyrosine, Taurine, Phenylalanine etc.) as well as proteins per se.

Further, wherein said minoxidil from a 5% source thereof, said mint oil, ginger oil, lavender oil, cumin oil and said castor oil from substantially 100% sources thereof are all present in equal amounts by volume, and in which said powdered horny goat weed; powdered *pueraria* lobate; powdered *tribulus terrestris*; powdered ashwagandha; powdered cayenne; powdered habenero; powdered green tea; powdered sage; powdered ginger; powdered stinging nettles; powdered *gingko biloba*; powdered myrrh; powdered alpha-hydroxy; powdered *aloe vera*; powdered wheat protein; powdered wheat starch; powdered casein; powdered keratin, powdered folic acid and powdered biotin are all present in equal amounts by weight.

It is also noted that in addition to the topical applications described above, practitioners of the methodology herein can also take oral supplements such as selected from the group of:

Saw Palmetto;

Horsetail;

*equisetum arvense;*

Folic acid;

Biotin;

Multi-vitamins; and

Niacin.

Inventor Welch mentions that of all the possible powdered selections, he has found approximately equal amount of powdered Horsetail, powdered *equisetum arvense*; powdered Saw Palmetto, powdered Stinging Nettles, powdered Casein, powdered Ginger and powdered Keratin are best for encouraging hair growth at the rearward portion of his scalp. And when applied to a dry scalp the mixture makes existing hair appear more-full. Further, the powdered Ginger seems more effective in frontal areas of hair challenged regions of his scalp.

It is probably to give a specific example of how to prepare liquids and powders for application in the present invention methodology. For instance, if a user decides to apply minoxidil from a 5% solution thereof, as well as castor oil and peppermint oil, he can measure out a half teaspoon of each and mix them together to form a volume of mixture. Then suppose the user decides to also apply powdered Horsetail, powdered *equisetum arvense*; powdered Saw Palmetto, powdered Stinging Nettles, powdered Casein, powdered Ginger and powdered Keratin. He can measure out approximately equal amounts of each by weight, and mix them together. Then a volume of said mixture of said powdered approximately equal to that of the liquids is measure out. In practice the user can apply both the volume of liquid and volume of powdered choices together, or can apply the volume of liquid and then apply the volume of powdered choices once the liquid has substantially dried. The later approach will tend to make existing hair look more-full. And if the methodology is practiced more than once between shampooing, then the next application of liquid will tend to dissolve the powdered selections and perhaps enhance their absorption into the hair challenged portion of the scalp. In interpreting Claims language this example should be kept in mind.

(It is noted that Shampoos are available on the Internet (Ebay) which are variously infused with Biotin and with Ginger and Saw Palmetto etc. A mixture of such shampoos is advised).'

Inventor Welch believes that when applying the LED/Laser produced electromagnetic radiation via a cap or helmet, one should orient it so that it primarily affects the rearward portion of the upper scalp. In his experience it is not as effective on forward areas.

Finally in this section, it is to be appreciated that it is important to protect one's eyes against the LED/laser light, mint oil and the other liquids and powders.

Forward Portion of Scalp

While the foregoing methodology is still basically applicable, in the inventor's experience getting hair regrowth results on the forward portion of the human male scalp is a far more difficult problem than in rearward regions. In particular, as previously alluded too, the inventor has noticed that application of electromagnetic radiation is not as successful when applied to the frontal area of his scalp, and that application of vibrations from a vibrator show possibly more success. Further, use of ginger oil and/or powdered ginger seems to be more successful in the frontal areas of the inventor's scalp than other selections. Therefore, the methodology might be amended to emphasize application of pure ginger oil or powdered ginger to the frontal regions of hair challenged regions of a human male scalp.

In the foregoing, Casein should be comprised of not only protein, but of Amino Acids, in particular Arginine and Cystein.

Where alcohol is added to the "Tea" described above, it is preferably ethyl or isopropyl alcohol, and while nominally present in a ratio of about 20:1 with water, can be present in as high as a 1:1 ratio.

While not investigated, it is noted that application of electric discharge and/or a magnetic field in the region of a human male hair challenged scalp might provide benefit.

Further, application of Transforming Growth Factor (TGF) containing, or other Cream or ointment etc. to the forward portion of the Scalp can be beneficial.

It is noted that use od Cayenne Pepper can cause light colored hair to be tinged orange. Use of "Just For Men" Control-GX can help overcome that effect.

It is also noted that application of warmth (as judged appropriate by user sensation—perhaps a moist 80-90 degrees Fahrenheit) to a hair challenged region of a human male scalp can also be practiced at any point in the methodology.

Inventor Welch attests that the results he has achieved are not as good as he would like, particularly in the frontal region of his scalp, but that being said the results achieved have been pretty good and they continue to improve slowly. Welch is 77 and much of his hair on the top of his head was dormant for decades. Being truthful it seems that some roots on the top of his head are not responding, at least not quickly. Hair on the edges of the top portion of his head, however, is responding and that edge is making its way centrally, slowly. Therefore, for best results it is advisable for younger people to get started earlier, before roots of hairs become very much damaged.

Finally, a Client and Former Co-Inventor on Teeth related Patents, (eg. 11,103,033) has suggested that a combination of Powdered or Liquid preparations of materials comprised of selections from the group: Sunflower Seeds, Sesame Seeds, Pumpkin Seeds, Chia Seeds, Wheat Germ and a Protein (eg. Raw Egg) can replace or supplement the many choices Claimed in this Application, both Externally and Internally. Also suggested, appropriate application(s) of a defoliating scrub might be of benefit in eliminating thickened scalp skin which can "bury" hair follicles, especially in older subjects.

Having hereby disclosed the subject matter of the present invention, it should be obvious that many modifications, substitutions and variations of the present invention are possible, therefore it is to be understood that the present invention can be practiced other than as specifically described and should be limited only by the appended Claims.

I claim:

1. A method of encouraging hair growth in male humans, comprising, in functional combination the steps of:
   a) providing a male human scalp comprising at least one hair challenged area;
   b) in a functional sequence, regarding said hair challenged area:
      1) providing and applying electromagnetic radiation;
      2) providing applying at least one powdered material; and
      3) providing and applying at least one liquid; and c) orally ingesting at least one naturally occurring hair growth encouraging substance.

2. A method as in claim 1 which step b) further comprises:
   4) Providing and applying a cream or ointment to said at least one hair challenged area;
   5) Shampooing said male human scalp with a shampoo comprising at least some of at least one selection from the group consisting of:
      mint;
      cayenne;
      caffeine;
      saw palmetto;
      *Equisetum arvense*; and
      biotin; and
   6) Providing a vibrator and apply vibrations to a hair challenged area of a provided scalp.

3. A method as in claim 1 in which step b) is practiced a multiplicity of times and in which the powdered material comprises at least some of at least one selection from the group consisting of:
   powdered horny goat weed;
   powdered *pueraria* lobate;
   powdered *tribulus terrestris;*
   powdered ashwagandha;
   powdered cayenne;
   powdered habenero;
   powdered green tea;
   powdered sage;
   powdered *gingko biloba;*
   powdered myrrh;
   powdered alpha-hydroxy;
   powdered *aloe vera;*
   powdered folic acid;
   powdered casein;
   powdered keratin;
   powdered biotin;
   powdered *ginseng* Root;
   powdered vetiver grass;
   powdered caffeine;
   powdered Co-enzyme Q;
   powdered folate;
   powdered gotukola leaf;
   powdered milk thistle;
   powdered African pygeum;
   powdered niacinamide;
   powdered *nigella sativa;*
   powdered *eclipta alba;*
   powdered centrella *asiatica;*
   powdered *phyllanthus emblica;*
   powdered turmeric;
   powdered curcumin;
   powdered pine bark;
   powdered casein;
   powdered buckthorn;
   powdered burdock;
   powdered chamomile;
   powdered comfrey;
   powdered hops;
   powdered rosemary;
   powdered thyme;
   powdered yarrow;
   powdered *yucca;*
   powdered *calendula;*
   powdered PABA;
   powdered peony root;
   powdered barley grass;
   powdered silicon dioxide;

powdered basil;

powdered MACA;

powdered *sarsaparilla;* powdered *muira* poama;

powdered pantothenic acid;

powdered Japanese knotweed;

powdered resveratrol;

powdered niacin;

powdered molybdenum;

powdered selenium;

powdered manganese;

powdered potassium;

powdered calcium;

powdered iron;

powdered copper;

powdered iodine;

powdered chromium;

powdered collagen;

powdered hydrolyzed collagen;

powdered keratin;

powdered solubilized keratin;

powdered black pepper;

powdered riboflavin; and powdered thiamine;

and the liquid is at least some of at least one selection from the group consisting of:

minoxidil infused liquid:

Mint infused liquid;

ginger infused liquid;

lavender infused liquid;

castor bean infused liquid;

jojoba infused liquid;

*malaleuca* infused liquid;

cumin infused liquid;

D-alpha tocopherol infused liquid;

caffeine infused liquid;

biotin infused liquid;

folic acid infused liquid;

*eucalyptus* liquid;

lemongrass liquid argan liquid;

clove liquid; and hyaluronic acid.

4. A method as in claim 2 in which step b) is practiced a multiplicity of times and the cream ointment contains transforming growth factor.

5. A method of encouraging hair growth in male humans, comprising, in functional combination the steps of:

a) providing a male human scalp comprising at least one hair challenged area;

b) shampooing said male human scalp with a shampoo comprising at least some of one selection from the group consisting of:

mint;

cayenne;

caffeine;

saw palmetto;

horsetail;

and biotin;

c) while still wet, applying at least one selection from the group consisting of:

powdered saw palmetto;

powdered horsetail;

powdered ginger;

powdered stinging nettles;

powdered cayenne;

powdered casein;

powdered keratin;

powdered folic acid;

powdered biotin;

Powdered Buckthorn;

Powdered Burdock;

Powdered Chamomile;

Powdered Comfrey;

Powdered Hops;

Powdered Rosemary;

Powdered Thyme;

Powdered Yarrow;

Powdered *Yucca;*

Powdered *Calendula;* powdered PABA;

powdered peony root;

powdered barley grass;

powdered silicon dioxide;

powdered basil;

powdered MACA;

powdered *sarsaparilla;* powdered *muira* poama;

powdered pantothenic acid;

powdered Japanese knotweed;

powdered resveratrol;

powdered niacin;

powdered molybdenum;

powdered selenium;

powdered manganese;

powdered potassium;

powdered calcium;

powdered iron;

powdered copper;

powdered iodine;

powdered chromium;

powdered collagen;

powdered hydrolyzed collagen;

powdered keratin;

powdered solubilized keratin;

powdered black pepper;

powdered riboflavin; and powdered thiamine;

and also while still wet, applying a mixture of substantially or exactly equal amounts of minoxidil solution from a 5% source and at least one selection from the group consisting of:

mint infused liquid;

ginger infused liquid;

lavender infused liquid;

castor bean infused liquid;

jojoba infused liquid;

*malaleuca* infused liquid;

cumin infused liquid;

D-alpha tocopherol infused liquid;

caffeine infused liquid;

biotin infused liquid;

folic acid infused liquid;

*eucalyptus* liquid;

lemongrass liquid argan liquid;

clove liquid; and hyaluronic acid;

d) while said male human scalp is still wet, or after it has dried, providing a multiple electromagnetic radiation source containing helmet or cap and applying electromagnetic radiation provided thereby to said at least one hair challenged area of said scalp while at least one of the multiple electromagnetic radiation sources are energized; and e) after said male human scalp has dried applying at least one selection from the group consisting of:
powdered horny goat weed;
powdered *pueraria* lobate;
powdered *tribulus* terrestris;
powdered ashwagandha;
powdered cayenne;
powdered habenero;
powdered green tea;
powdered sage;
powdered *gingko biloba;*
powdered myrrh;
powdered alpha-hydroxy;
powdered *aloe vera;*
powdered folic acid;
powdered casein;
powdered keratin;
powdered biotin;
powdered *ginseng* Root;
powdered vetiver grass;
powdered caffeine;
powdered Co-enzyme Q;
powdered folate;
powdered gotukola leaf;
powdered milk thistle;
powdered African pygeum;
powdered niacinamide;
powdered *nigella sativa;*
powdered *eclipta alba;*
powdered centrella *asiatica;*
powdered *phyllanthus emblica;*
powdered turmeric;
powdered curcumin; and
powdered pine bark;
powdered casein;
powdered buckthorn;
powdered burdock;
powdered chamomile;
powdered comfrey;
powdered hops;
powdered rosemary;
powdered thyme;
powdered yarrow;
powdered *yucca;*
powdered *calendula;*
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;

powdered iodine;
powdered chromium;
powdered collagen;
powdered hydrolyzed collagen;
powdered keratin;
powdered solubilized keratin;
powdered black pepper;
powdered riboflavin; and
powdered thiamine;

f) at some point after step a) providing and applying a cream or ointment to said at least one hair challenged area; and g) orally ingesting at least one naturally occurring hair growth encouraging substance.

6. A method of encouraging hair growth in male humans, comprising the steps of:

a) providing and shampooing a scalp of a human male having at least one hair challenged area in need of hair regrowth, along with any hair present, with a shampoo comprising at least some of at least one selection from the group consisting of:
mint;
cayenne;
caffeine;
saw palmetto;
*equisetum arvense*; and
biotin;
present therein;

b) before drying said scalp providing and applying a mixture of substantially or exactly equal amounts of at least two selections from the group consisting of:
powdered saw palmetto;
powdered horsetail;
powdered ginger;
powdered stinging nettles;
powdered cayenne;
powdered casein;
powdered keratin;
powdered folic acid;
powdered biotin;
to said at least one hair challenged area of said provided scalp;

c) providing and applying a mixture of substantially or exactly equal amounts of minoxidil solution from a 5% source and at least one selection from the group consisting of:
mint infused liquid;
ginger infused liquid;
lavender infused liquid;
castor bean infused liquid;
jojoba infused liquid;
*malaleuca* infused liquid;
cumin infused liquid;
D-alpha tocopherol infused liquid;
caffeine infused liquid;
biotin infused liquid;
folic acid infused liquid;
*eucalyptus* liquid;
lemongrass liquid argan liquid;
clove liquid; and
hyaluronic acid;
to said at least one hair challenged area of said provided scalp;

d) said method further comprising, drying said scalp and any hair present, then providing and applying a mixture of substantially or exactly equal amounts of at least two selections from the group consisting of:

powdered saw palmetto;
powdered horsetail;
powdered ginger;
powdered stinging nettles;
powdered cayenne;
powdered casein;
powdered keratin;
powdered folic acid;
to said at least one hair challenged area of said provided
scalp;
e) providing a multiple electromagnetic radiation source
containing helmet or cap and applying electromagnetic
radiation provided thereby to said at least one hair
challenged area of said scalp while at least one of the
multiple electromagnetic radiation sources are ener-
gized; and
f) at some point after step a) providing and a cream or
ointment to said at least one hair challenged area; and
g) orally ingesting at least one naturally occurring hair
growth encouraging substance.
7. A method as in claim 1 which comprises orally ingest-
ing at least some of at least one selection from the group
consisting of:
saw palmetto;
horsetail;
ginger;
stinging nettles;
casein;
keratin;
peppermint;
ginger;
lavender oil;
vitamin E;
biotin;
cumin;
castor oil;
jojoba oil;
*malaleuca* oil;
cumin oil;
D-alpha tocopherol;
fenugreek seed;
horny goat weed;
*pueraria* lobate;
*tribulus* terrestris;
ashwagandha;
cayenne;
habenero;
green tea;
sage;
*gingko* biloba;
myrrh;
alpha-hydroxy;
*aloe vera;*
folic acid;
biotin;
*ginseng* Root;
vetiver grass;
caffeine;
Co-enzyme Q;
folate;
gotukola leaf;
milk thistle;
African pygeum;
niacinamide;
*nigella* satavia;
*eclipta alba;*
centrella *asiatica;*

*phyllanthus emblica;*
turmeric;
curcumin;
pine bark;
caesin;
cayenne;
powdered buckthorn;
powdered burdock;
powdered chamomile;
powdered comfrey;
powdered hops;
powdered rosemary;
powdered thyme;
powdered yarrow;
powdered *yucca;*
powdered *calendula;*
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
powdered black pepper;
powdered riboflavin; and
powdered thiamine;
at least one vitamin selected from the group of: A; C; D1;
D2; D3; B3; B5, K and B12;
at least one amino acid selected from the group of:
alanine; cysteine; tryptophan; glutamic acid; histidine;
isoleucine; tryptophan; arginine; aspartic acid; threo-
nine; tyrosine; glycine; leucine; proline; lysine; methio-
nine; serine; valine and phenylalanine.
8. A method as in claim 5 which further comprises orally
ingesting at least some of at least one selection from the
group consisting of:
saw palmetto;
horsetail;
*equisetum* arvense;
ginger;
stinging nettles;
casein;
keratin;
peppermint;
ginger;
lavender oil;
vitamin E;
biotin;
cumin;

castor oil;
jojoba oil;
*malaleuca* oil;
cumin oil;
D-alpha tocopherol;
fenugreek seed;
horny goat weed;
*pueraria* lobate;
*tribulus* terrestris;
ashwagandha;
cayenne;
habenero;
green tea;
sage;
*gingko* biloba;
myrrh;
alpha-hydroxy;
*aloe vera;*
folic acid;
biotin;
*ginseng* Root;
vetiver grass;
caffeine;
Co-enzyme Q;
folate;
gotukola leaf;
milk thistle;
African pygeum;
niacinamide;
*nigella* satavia;
*eclipta alba;*
centrella *asiatica;*
*phyllanthus emblica;*
turmeric;
curcumin;
pine bark;
caesin;
cayenne;
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
powdered black pepper;
powdered riboflavin; and
powdered thiamine;

at least one vitamin selected from the group of: A; C; D1;
D2; D3; B3; B5, K and B12;
at least one amino acid selected from the group of:
alanine; cysteine; tryptophan; glutamic acid; histidine;
isoleucine; tryptophan; arginine; aspartic acid; threo-
nine; tyrosine; glycine; leucine; proline; lysine; methio-
nine; serine; valine and phenylalanine.

9. A method as in claim 6 which further comprises orally
ingesting at least some of at least one selection from the
group consisting of:
saw palmetto;
horsetail;
ginger;
stinging nettles;
casein;
keratin;
peppermint;
ginger;
lavender oil;
vitamin E;
biotin;
cumin;
castor oil;
jojoba oil;
*malaleuca* oil;
cumin oil;
D-alpha tocopherol;
fenugreek seed;
horny goat weed;
*pueraria* lobate;
*tribulus* terrestris;
ashwagandha;
cayenne;
habenero;
green tea;
sage;
*gingko* biloba;
myrrh;
folic acid;
biotin;
*ginseng* Root;
vetiver grass;
caffeine;
Co-enzyme Q;
folate;
gotukola leaf;
milk thistle;
African pygeum;
niacinamide;
*nigella* satavia;
*eclipta alba;*
centella *asiatica;*
*phyllanthus emblica;*
turmeric;
curcumin;
pine bark;
caesin;
cayenne;
powdered PABA;
powdered peony root;
powdered barley grass;
powdered silicon dioxide;
powdered basil;
powdered MACA;
powdered *sarsaparilla;*
powdered *muira* poama;
powdered pantothenic acid;

powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
powdered black pepper;
powdered riboflavin; and
powdered thiamine;
  at least one vitamin selected from the group of: A; C; D1; D2; D3; B3; B5, K and B12;
  at least one amino acid selected from the group of: alanine; cysteine; tryptophan; glutamic acid; histidine; isoleucine; tryptophan; arginine; aspartic acid; threonine; tyrosine; glycine; leucine; proline; lysine; methionine; serine; valine and phenylalanine.

10. A method as in claim 5 which further comprises providing a provided vibrator and apply vibrations to a hair challenged area of a provided scalp.

11. A method as in claim 6 which further comprises providing a vibrator and apply vibrations to a hair challenged area of a provided scalp.

12. A method as in claim 5 in which all selections in the groups b) and c) are present in substantially, or exactly equivalent amounts in each group.

13. A method as in claim 6 in which all selections in the groups b) and c) are present in substantially, or exactly equivalent amounts in each group.

14. A method as in claim 1 in which electromagnetic radiation is applied for at least five minutes.

15. A method as in claim 1 in which the mint is peppermint oil.

16. A method as in claim 2 in which the mint is peppermint comprising at least one percent methanol.

17. A method as in claim 5 in which the mint is peppermint comprising at least one percent methanol.

18. A method as in claim 1 in which the step b) 3) further comprises a liquid "tea" made from at least one selection from the group consisting of:
  powdered horny goat weed;
  powdered *pueraria* lobate;
  powdered *tribulus* terrestris;
  powdered ashwagandha;
  powdered cayenne;
  powdered habenero;
  powdered green tea;
  powdered sage;
  powdered *gingko* biloba;
  powdered myrrh;
  powdered alpha-hydroxy;
  powdered *aloe vera;*
  powdered folic acid;
  powdered casein;
  powdered keratin;
  powdered biotin;
  powdered *ginseng* Root;
  powdered vetiver grass;

powdered caffeine;
powdered Co-enzyme Q;
powdered folate;
powdered gotukola leaf;
powdered milk thistle;
powdered African pygeum;
powdered niacinamide;
powdered *nigella sativa;*
powdered *eclipta alba;*
powdered centrella *asiatica;*
powdered *phyllanthus emblica;*
powdered turmeric;
powdered curcumin;
powdered pine bark; and
powdered casein;
powdered buckthorn;
powdered burdock;
powdered chamomile;
powdered comfrey;
powdered hops;
powdered rosemary;
powdered thyme;
powdered yarrow;
powdered *yucca;*
powdered *calendula*
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
powdered black pepper;
powdered riboflavin; and
powdered thiamine.

19. A method as in claim 5 in which the step c) further comprises a liquid "tea" made from at least one selection from the group consisting of:
  powdered horny goat weed;
  powdered *pueraria* lobate;
  powdered *tribulus* terrestris;
  powdered ashwagandha;
  powdered cayenne;
  powdered habenero;
  powdered green tea;
  powdered sage;
  powdered *gingko* biloba;
  powdered myrrh;
  powdered alpha-hydroxy;

powdered *aloe vera;*
powdered folic acid;
powdered casein;
powdered keratin;
powdered biotin;
powdered *ginseng* Root;
powdered vetiver grass;
powdered caffeine;
powdered Co-enzyme Q;
powdered folate;
powdered gotukola leaf;
powdered milk thistle;
powdered African pygeum;
powdered niacinamide;
powdered *nigella sativa;*
powdered *eclipta alba;*
powdered centrella *asiatica;*
powdered *phyllanthus emblica;*
powdered turmeric;
powdered curcumin;
powdered pine bark;
powdered casein;
powdered buckthorn;
powdered burdock;
powdered chamomile;
powdered comfrey;
powdered hops;
powdered rosemary;
powdered thyme;
powdered yarrow;
powdered *yucca;*
powdered *calendula;*
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
powdered black pepper;
powdered riboflavin; and
powdered thiamine.

20. A method as in claim 6 in which the step c) further comprises a liquid "tea" made from at least one selection from the group consisting of:
powdered horny goat weed;
powdered *pueraria* lobate;
powdered *tribulus* terrestris;
powdered ashwagandha;

powdered cayenne;
powdered habenero;
powdered green tea;
powdered sage;
powdered *gingko* biloba;
powdered myrrh;
powdered alpha-hydroxy;
powdered *aloe vera;*
powdered folic acid;
powdered casein;
powdered keratin;
powdered biotin;
powdered *ginseng* Root;
powdered vetiver grass;
powdered caffeine;
powdered Co-enzyme Q;
powdered folate;
powdered gotukola leaf;
powdered milk thistle;
powdered African pygeum;
powdered niacinamide;
powdered *nigella sativa;*
powdered *eclipta alba;*
powdered centrella *asiatica;*
powdered *phyllanthus emblica;*
powdered turmeric;
powdered curcumin;
powdered pine bark;
powdered casein;
powdered buckthorn;
powdered burdock;
powdered chamomile;
powdered comfrey;
powdered hops;
powdered rosemary;
powdered thyme;
powdered yarrow;
powdered *yucca;*
powdered *calendula;*
powdered PABA;
powdered peony root;
powdered barley grass;
powdered silicon dioxide;
powdered basil;
powdered MACA;
powdered *sarsaparilla;*
powdered *muira* poama;
powdered pantothenic acid;
powdered Japanese knotweed;
powdered resveratrol;
powdered niacin;
powdered molybdenum;
powdered selenium;
powdered manganese;
powdered potassium;
powdered calcium;
powdered iron;
powdered copper;
powdered iodine;
powdered chromium;
powdered collagen;
powdered hydrolyzed collagen;
powdered keratin;
powdered solubilized keratin;
powdered black pepper;
powdered riboflavin; and
powdered thiamine.

21. A method as in claim 1, wherein the sequence of practicing the categories in step b) is selected from the group consisting of:

1), 3) 2);

1), 2) 3);

3), 1,2).

22. A method as in claim 2, wherein the sequence of practicing the categories in step b) is: 5), 3), 1), 2), 4) and 6).

23. A method of encouraging hair growth in male humans, comprising, in functional combination the steps of:

a) providing a male human scalp comprising at least one hair challenged area;

b) in a functional sequence, regarding said hair challenged area:

1) Providing and applying minoxidil;

2) Providing and applying electromagnetic radiation; and

3) Providing and applying a liquid "tea" made from at least one selection from the group consisting of:

powdered horny goat weed;

powdered *pueraria* lobate;

powdered *tribulus* terrestris;

powdered ashwagandha;

powdered cayenne;

powdered habenero;

powdered green tea;

powdered sage;

powdered *gingko* biloba;

powdered myrrh;

powdered alpha-hydroxy;

powdered *aloe vera;* powdered folic acid;

powdered casein;

powdered keratin;

powdered biotin;

powdered *ginseng* Root;

powdered vetiver grass;

powdered caffeine;

powdered Co-enzyme Q;

powdered folate;

powdered gotukola leaf;

powdered milk thistle;

powdered African pygeum;

powdered niacinamide;

powdered *nigella sativa;* powdered *eclipta alba;* powdered centrella *asiatica;* powdered *phyllanthus emblica;* powdered turmeric;

powdered curcumin;

powdered pine bark;

powdered casein;

powdered buckthorn;

powdered burdock;

powdered chamomile;

powdered comfrey;

powdered hops;

powdered rosemary;

powdered thyme;

powdered yarrow;

powdered *yucca;* powdered *calendula;* powdered PABA;

powdered peony root;

powdered barley grass;

powdered silicon dioxide;

powdered basil;

powdered MACA;

powdered *sarsaparilla;* powdered *muira* poama;

powdered pantothenic acid;

powdered Japanese knotweed;

powdered resveratrol;

powdered niacin;

powdered molybdenum;

powdered selenium;

powdered manganese;

powdered potassium;

powdered calcium;

powdered iron;

powdered copper;

powdered iodine;

powdered chromium;

powdered collagen;

powdered hydrolyzed collagen;

powdered keratin;

powdered solubilized keratin;

powdered black pepper;

powdered riboflavin; and powdered thiamine.

\* \* \* \* \*